United States Patent [19]
May et al.

[11] Patent Number: 6,140,373
[45] Date of Patent: Oct. 31, 2000

[54] PROPOFOL COMPOSITION

[75] Inventors: Thomas May, Grayslake; John Hofstetter, Vernon Hills; Kathleen L. Olson, Chicago; Sukumaran K. Menon, Gurnee; Bernard A. Mikrut, Lake Bluff; Clayton S. Ovenshire, Park Ridge; Lawrence John Rhodes, Lindenhurst; Earl R. Speicher, Buffalo Grove; James R. Waterson, Gurnee, all of Ill.

[73] Assignee: Abbott Laboratories, Abbott Park, Ill.

[21] Appl. No.: 09/178,347

[22] Filed: Oct. 23, 1998

[51] Int. Cl.⁷ .................................................. A61K 31/55
[52] U.S. Cl. .............................................................. 514/731
[58] Field of Search .............................................. 514/731

[56] References Cited

U.S. PATENT DOCUMENTS 5,714,520  2/1998  Jones et al. ............................... 514/731

OTHER PUBLICATIONS

Database Chemical ABstracts on STN, AN 1976:160061, Haque et al, "Cell envelopes of gram negative bacteria: composition, response to chelating agents and susceptibility of whole cells to antibacterial agents", J. Appl. Bacteriol. (Jan. 1976), 40(1), 89–99.

Database Chemical Abstracts on STN, AN 1986:622538, Karabit et al, "Studies on the evaluation of preservative efficacy. I. The determination of antimicrobial characteristics of benzyl alcohol", J. Clin. Hosp. Pharm. (Jan. 1986), 11(4), 281–9.

*Primary Examiner*—Keith D. MacMillan
*Attorney, Agent, or Firm*—Gregory W. Steele

[57] ABSTRACT

The present invention is directed to a sterile pharmaceutical composition comprising a propofol containing oil-in-water emulsion formulation having as an antimicrobial agent, a member selected from the group consisting of benzyl alcohol and ethylene diamine tetra acetic acid; benzethonium chloride; and benzyl alcohol and sodium benzoate.

24 Claims, No Drawings

PROPOFOL COMPOSITION

FIELD OF THE INVENTION

The present Invention relates to pharmaceutical compositions containing 2,6-diisopropylphenol.

BACKGROUND OF THE INVENTION

Propofol (26-diisopropylphenol) an injectable anesthetic which has hypnotic properties and can be used to induce and maintain general anesthesia and for sedation. Injectable anesthetics such as propofol are administered directly into the bloodstream. This results in a rapid onset of anesthesia influenced almost entirely by the rate at which the anesthetic agent crosses the blood-brain barrier. Therefore, the anesthetic agent must have sufficient lipid solubility to be able to cross this barrier and depress the relevant mechanisms of the brain. Propofol is poorly water soluble and therefore is generally formulated as an emulsion. Propofol containing emulsions have been shown to support microbial growth. Therefore it is desirable to formulate propofol emulsions in a manner in which microbial growth is prevented. EDTA (ethylene diamine tetraacetic acid) has been shown to delay, but not prevent, the onset of microbial growth in propofol emulsions. See U.S. Pat. No. 5,714,520.

Accordingly it is an object of the present invention to provide a propofol containing pharmaceutical composition that provides antimicrobial benefits above that found in existing compositions and/or prevents the onset of microbial growth in such compositions.

SUMMARY OF THE INVENTION

The present invention is directed to a sterile pharmaceutical composition comprising a propofol containing oil-in-water emulsion formulation having as an antimicrobial agent, a member selected from the group consisting of benzyl alcohol and ethylene diamine tetraacetic acid; benzethonium chloride; and benzyl alcohol and sodium benzoate.

DETAILED DESCRIPTION OF THE INVENTION

The term "anti-microbial" means an agent which delays onset or retards rate of growth to less than 1 logarithmic increase over a 24 hour period as compared to an unpreserved formulation.

The composition of the present invention comprises an oil in water emulsion in which the 2,6-diisopropylphenol, either alone or dissolved in a water immiscible solvent, for example a vegetable oil, is emulsified with water by means of surfactant.

Typically the solvent is an oil such as soy bean oil, safflower oil, cottonseed oil, corn oil, sunflower oil, arachis oil, castor oil, or olive oil. Preferably the oil is soybean oil. Alternatively the solvent can be an ester of a medium or long chain fatty acid, for example a mono-,di-, or triglyceride; or a compound such as ethyl oleate, isopropyl myristate, isopropyl palmitate, a glycerol ester or a polyoxyl hydrogenated castor oil. Other suitable solvents may be marine oils, for example cod liver or other fish derived oils, or fractionated oils, such as fractionated coconut oil or modified soybean oil. The composition of present invention may also comprise a mixture of two or more of the above water immiscible solvents.

The 2,6-diisopropylphenol, either alone or dissolved in the water immiscible solvent, is emulsified with the aid of a surfactant. Suitable surfactants include synthetic non-ionic surfactants, for example ethoxylated ethers and esters and polypropylene polyethylene block copolymers, and phosphatides, as for example egg and soy phosphatides. Preferably, the surfactant is egg phosphatide.

Preferred compositions of the present invention comprise from 0.1 to 5.0% by weight, preferably 1 to 2% by weight, and most preferably 2% by weight of 2,6-diisopropylphenol; from to 2 to 30% by weight, preferably 10 to 20% by weight of a nonionic surfactant; from 2 to 90% by weight of a water immiscible solvent, and the balance of the composition being water.

The antimicrobial systems utilized in the compositions of the present invention are selected from the group consisting of benzyl alcohol and ethylene diamine tetraacetic acid; benzethonium chloride; and benzyl alcohol and sodium benzoate. The concentration of the antimicrobial agents in the final composition will vary depending on the particular agent or agents selected. For instance in a preferred composition of the invention the amount of benzyl alcohol is in the range of about 0.0175% to 0.9% (w/v), more preferably about 0.07% to about 0.45%, most preferred in the range of 0.15%. In an alternate preferred composition of the invention, the amount of benzyl alcohol is about 0.07% to about 0.9%, optionally including an amount of EDTA of about 0.005%. Yet another embodiment provides a composition including an amount of benzethonium chloride of about 0.1% to about 0.1%. Optionally, the composition of the present invention include 0.07% nb. The most preferred compositions of the present invention include benzyl alcohol and nb. The compositions of the present invention may be prepared by conventional processes as for example that disclosed in U.S. Pat. No. 5,714,520.

The compositions of the present invention can also contain pH adjusting agents such as sodium hydroxide so they can be formulated at a physiologically neutral pH.

The compositions of the present invention may also be made isotonic by the incorporation of a suitable additive such as glycerol.

A particularly preferred composition of the present invention is as set forth below.

TABLE 1

| Component | (weight percent) | | |
|---|---|---|---|
| | Broad Range | Preferred Range | Particularly Preferred Amount |
| 2,6-diisopropylphenol | 0.1–5.0 | 1.0–2.0 | 1.0 |
| Soybean Oil | 1–30 | 10–30 | 10 |
| Egg Phosphatide | 0.2–2.0 | 0.7–2.0 | 1.2 |
| Benzyl alcohol | 0.0175–0.9 | 0.07–0.45 | 0.15 |
| nb | 0.07 | 0.07 | 0.07 |
| Glycerol | | | 2.25 |
| Sodium Hydroxide | q.s. | q.s. | q.s. |
| Water for Injection | to 100 | to 100 | to 100 |

The compositions of the present invention may be used for the induction of anesthesia prior to maintenance with a conventional inhalation anesthetic or they may used as a sole anesthetic agent for short duration or by repeated administration or by continuous infusion they may be use as a sole anesthetic agent of longer duration.

The invention is illustrated by the following representative examples:

EXAMPLE 1

The compositions of the present invention may be formulated following procedures well known to those skilled in the art. Specific reference is made to U.S. Pat. No. 5,714,520 which is hereby incorporated by reference.

EXAMPLE 2

Solutions of 0.45% benzyl alcohol/0.005% EDTA, 0.035%benzyl alcohol/0.005% EDTA, 0.45% benzyl alcohol/0.07%nb, and 0.35% benzyl alcohol/0.07%nb were passed through a 0.45 micron filter and tested by the USP 23 preservative effectiveness test as described in United States Pharmacopoeia 23-NF 18, 1995 Ed., Chapter 51, which is incorporated herein by reference. Briefly, this involves inoculating the test solution with $10^5$ to $10^6$ test organisms per milliliter and then determining the number of surviving organisms after 7, 14, 21, and 28 days incubation at 20–25° C. using standard microbiological methods. Day 0 data is not required by USP 23 but was included in this study. A filtration and was method was used to remove the inactivating agents for purposes of recovering the microorganisms, but other equivalent methods can also be validated for use. The USP test organisms include the bacteria *Staphylococcus aureus, Escherichia coli,* and *Pseudomonoas aeruginosa,* a yeast (*Candida albicans*), and a mold (*Aspergillus niger*). In order to meet the criteria of the USP 23 preservative effectiveness test, the bacteria must demonstrate a 90% (1 logarithmic) reduction at Day 7 and a 99.9% reduction (3 logarithmic) reduction at Day 14 from the initial inoculum level. The initial inoculum level can either be calculated knowing the stock culture concentration or by using a buffer control instead of the test solution. The results, using formulations which are 10% fat emulsions, are given below in Tables 2 through 5 where the number reported in the number of organisms pre milliliter. ND means not detected, i.e., below the levels of detection by the assay.

TABLE 2

(0.45% benzyl alcohol/0.005% EDTA)

| | Organism | | | | |
|---|---|---|---|---|---|
| Time | A. niger | C. albicans | E. coli | P. aeruginosa | S. aureus |
| Inoculum per ml product | 390,000 | 440,000 | 750,000 | 460,000 | 610,000 |
| 0 Hr. | 300,000 | 300 | <10 ND | <10 ND | <10 ND |
| Day 7 | 210,000 | 340,000 | 680 | 3,000 | 47,000 |
| Day 14 | 210,000 | 350,000 | 190 | 200 | 7,200 |
| Day 21 | 3,400 | 270,000 | 40 | 60 | 4,300 |
| Day 28 | 130 | 105,000 | 10 | 10 | 1,020 |

TABLE 3

(0.035% BENZYL ALCOHOL/0.005 EDTA)

| | Organism | | | | |
|---|---|---|---|---|---|
| Time | A. niger | C. albicans | E. coli | P. aeruginosa | S. aureus |
| Inoculum per ml product | 390,000 | 440,000 | 750,000 | 460,000 | 610,000 |
| 0 Hr. | 300,000 | 310,000 | 360,000 | 310,000 | 430,000 |
| Day 7 | 300,000 | 330,000 | 40 | 105,000 | 36,000 |
| Day 14 | 210,000 | 310,000 | <10 ND | 68,000 | 3,500 |

TABLE 3-continued (0.035% BENZYL ALCOHOL/0.005 EDTA)

| | Organism | | | | |
|---|---|---|---|---|---|
| Time | A. niger | C. albicans | E. coli | P. aeruginosa | S. aureus |
| Day 21 | 120,000 | 320,000 | <10 ND | 67,000 | 740 |
| Day 28 | 29,000 | 110,000 | >10 ND | 38,000 | 170 |

TABLE 4

(0.45 benzyl alcohol/0.07 nb)

| | Organism | | | | |
|---|---|---|---|---|---|
| Time | A. niger | C. albicans | E. coli | P. aeruginosa | S. aureus |
| Inoculum per ml product | 390,000 | 440,000 | 750,000 | 460,000 | 610,000 |
| 0 Hr. | 260,000 | 340,000 | 380,000 | 440,000 | 390,000 |
| Day 7 | 260,000 | 390,000 | 86,000 | 101,000 | 30,000 |
| Day 14 | 29,000 | 350,000 | 62,000 | 14,900 | 1,350 |
| Day 21 | 22,000 | 203,000 | 80,000 | 2,800 | 100 |
| Day 28 | 290 | 87,000 | 76,000 | 150 | 10 |

TABLE 5

(0.035 BA/0.07% NB)

| | Organism | | | | |
|---|---|---|---|---|---|
| Time | A. niger | C. albicans | E. coli | P. aeruginosa | S. aureus |
| Inoculum per ml product | 390,000 | 440,000 | 750,000 | 460,000 | 610,000 |
| 0 Hr. | 370,000 | 450,000 | 420,000 | 550,000 | 520,000 |
| Day 7 | 250,000 | 530,000 | 8,800,000 | 3,500,000 | 310,000 |
| Day 14 | 130,000 | 410,000 | 7,100,000 | 3,400,000 | 92,000 |
| Day 21 | 41,000 | 440,000 | 5,800,000 | 30,000 | 49,000 |
| Day 28 | 13,000 | 300,000 | 2,180,000 | 7,000 | 22,100 |

EXAMPLE 3

The antimicrobial properties of various Propofol formulations were determined by a spiked hold time study. Briefly, a Propofol formulation is inoculated to achieve approximately 100 organisms per 10 mL sample. The organisms used include *Staphylococcus aureus, Pseudomonas aeruginosa, Escherichia coli, Candida albicans, Bacillus subtilis, Aspergillus niger,* and *Clostridium sporogenes.* The inoculated samples are held for various times and then filtered in duplicate. The filters are washed with buffer and then placed on appropriate agar growth media. The antimicrobial agents should reduce the growth rate such that there is less than a 1 logarithm increase within a 24 hour period.

*C. albicans* presented the most resistance to the preservative system. The *C. albicans* results from the spiked hold time study are shown below for various propofol formulations. *E. coli, P. aeruginosa,* and *B. subtilis* also demonstrated some resistance to the antimicrobial agents (data not shown). The remaining test organisms increased less than 2-fold over the 7 day test period. The results are shown in cfu/mL. A value of >300indicates too numerous to count; these data points may still meet the acceptance criteria of less than 1 logaritmic increase. In the Tables, BA=Benzyl Alcohol, NB=Sodium Benzoate. The percent of benzyl alcohol is indicated in w/v for each formulation. The percents Sodium benzoate, when present, is 0.07% (w/v).

| Formulation | 0 hours 1 | 24 hours | 48 hours 1 | 7 days 1 |
|---|---|---|---|---|
| 0.45 BA/NB | 37 | 35 | 28 | 56 |
| 0.15 BA only | 59 | 102 | >300 | >300 |
| 0.15 BA/NB | 59 | 45 | >300 | >300 |
| 0.13 BA/NB | 66 | 57 | >300 | >300 |
| 0.10 BA/NB | 53 | 59 | >300 | >300 |
| 0.07 BA/NB | 34 | 120 | >300 | >300 |
| 0.035 BA/NB | 33 | 125 | >300 | >300 |
| 0.0175 BA/NB | 38 | 185 | >300 | >300 |

What is claimed is:

1. A sterile oil-in-water emulsion pharmaceutical composition comprising:
   from 0.1 to 5.0 weight percent propofol;
   from 2.0 to 30 weight percent solvent;
   from 0.2 to 2.0 weight percent surfactant;
   2.25 weight percent glycerol;
   from 0.0175 to 0.9 weight percent of benzyl alcohol alone or in combination with sodium benzoate as an antimicrobial agent and the balance of the composition being water.

2. The composition of claim 1 having
   from 1.0 to 2.0 weight percent propofol;
   from 1.0 to 30 weight percent solvent;
   from 0.7 to 2.0 weight percent surfactant;
   from 0.07 to 0.45 weight percent benzyl alcohol; and,
   0.07 weight percent sodium benzoate.

3. The composition of claim 2 having
   1.0 weight percent propofol;
   10 weight percent solvent;
   1.2 weight percent surfactant;
   0.15 weight percent benzyl alcohol; and,
   0.07 weight percent sodium benzoate.

4. The composition according to claim 1 wherein the propofol is emulsified by means of a surfactant.

5. The composition according to claim 4 wherein the surfactant is an ethoxylated ether or ester, a polypropylene polyethylene block copolymer or a phosphatide.

6. The composition according to claim 5 wherein the surfactant is egg phosphatide.

7. The composition according to claim 1 wherein the propofol is dissolved in a water-immiscible solvent.

8. The composition according to claim 7 wherein the solvent is soybean oil, safflower oil, cottonseed oil, corn oil, sunflower oil, arachis oil, castor oil or olive oil.

9. The composition of claim 4 wherein the solvent is soybean oil.

10. The composition of claim 1 wherein sodium benzoate is in combination with benzyl alcohol.

11. The composition according to claim 10 wherein the propofol is emulsified by means of a surfactant.

12. The composition according to claim 11 wherein the surfactant is an ethoxylated ether or ester, a polypropylene polyethylene block copolymer or a phosphatide.

13. The composition according to claim 12 wherein the surfactant is egg phosphatide.

14. The composition according to claim 10 wherein the propofol is dissolved in a water-immiscible solvent.

15. The composition according to claim 14 wherein the solvent is soybean oil, safflower oil, cottonseed oil, corn oil, sunflower oil, arachis oil, castor oil or olive oil.

16. The composition according to claim 15 wherein the solvent is soybean oil.

17. A method of inducing anesthesia or sedation comprising administering to a patient in need thereof an anesthesia- or sedation-inducing amount of a sterile pharmaceutical composition comprising a propofol containing oil-in-water emulsion having as an antimicrobial agent benzyl alcohol alone or in combination with sodium benzoate.

18. A method of maintaining anesthesia or sedation comprising administering to a patient in need thereof an anesthesia- or sedation- maintaining amount of a sterile pharmaceutical composition comprising a propofol containing oil-in-water emulsion having as an antimicrobial agent benzyl alcohol alone or in combination with sodium benzoate.

19. A method of inducing anesthesia or sedation comprising administering to a patient in need thereof an anesthetic or sedation inducing amount of a sterile oil-in-water emulsion pharmaceutical composition comprising:
   from 0.1 to 5.0 weight percent propofol;
   from 2.0 to 30 weight percent solvent;
   from 0.2 to 2.0 weight percent surfactant;
   from 2.0 to 3.0 weight percent glycerol;
   from 0.0175 to 0.9 weight percent of benzyl alcohol and sodium benzoate as an antimicrobial agent; and
   the balance of the composition being water.

20. The method of claim 19 wherein the pharmaceutical composition is
   1.0 weight percent propofol;
   10 weight percent solvent;
   1.2 weight percent surfactant;
   0.15 weight percent benzyl alcohol; and,
   0.07 weight percent sodium benzoate.

21. The method of claim 20 wherein the solvent is soybean oil and the surfactant is egg phosphatide.

22. A method of maintaining anesthesia or sedation comprising administering to a patient in need thereof an anesthesia- or sedation- maintaining amount of a sterile oil-in-water emulsion pharmaceutical composition comprising:
   from 0.1 to 5.0 weight percent propofol;
   from 2.0 to 30 weight percent solvent;
   from 0.2 to 2.0 weight percent surfactant;
   from 2.0 to 3.0 weight percent glycerol;
   from 0.0175 to 0.9 weight percent of benzyl alcohol and sodium benzoate as an antimicrobial agent; and
   the balance of the composition being water.

23. The method of claim 22 wherein the pharmaceutical composition is
   1.0 weight percent propofol;
   10 weight percent solvent;
   1.2 weight percent surfactant;
   0.15 weight percent benzyl alcohol; and,
   0.07 weight percent sodium benzoate.

24. The method of claim 23 wherein the solvent is soybean oil and the surfactant is egg phosphatide.

* * * * *

UNITED STATES PATENT AND TRADEMARK OFFICE
CERTIFICATE OF CORRECTION

PATENT NO.    : 6,140,373
DATED         : October 31, 2000
INVENTOR(S)   : Thomas May et al.

It is certified that error appears in the above-identified patent and that said Letters Patent is hereby corrected as shown below:

Column 5,
Line 31, replace "1.0 to 30" with -- 10 to 30 --.
Line 55, replace "of claim 4" with -- of claim 8 --.

Signed and Sealed this

Twenty-fourth Day of December, 2002

JAMES E. ROGAN
*Director of the United States Patent and Trademark Office*